United States Patent [19]

Tomkiel

[11] Patent Number: 4,927,416
[45] Date of Patent: May 22, 1990

[54] USER-PROTECTIVE HYPODERMIC SYRINGE HOLDER

[75] Inventor: Stanley Tomkiel, South Hempstead, N.Y.

[73] Assignee: National Medical Device Corporation, Valley Stream, N.Y.

[21] Appl. No.: 230,796

[22] Filed: Aug. 10, 1988

Related U.S. Application Data

[63] Continuation-in-part of Ser. No. 127,689, Dec. 2, 1987, abandoned.

[51] Int. Cl.⁵ ............................................. A61M 5/32
[52] U.S. Cl. .................................... 604/198; 604/263
[58] Field of Search ............... 604/198, 195, 192, 187, 604/263, 136

[56] References Cited

U.S. PATENT DOCUMENTS

| | | |
|---|---|---|
| 3,702,608 | 11/1972 | Tibbs ................................... 604/136 |
| 3,890,971 | 6/1975 | Leeson et al. . |
| 4,425,120 | 1/1984 | Sampson et al. . |
| 4,631,057 | 12/1986 | Mitchell ............................. 604/198 |
| 4,639,249 | 1/1987 | Larson ................................ 604/198 |
| 4,659,330 | 4/1987 | Nelson et al. . |
| 4,664,654 | 5/1987 | Strauss . |
| 4,702,738 | 10/1987 | Spencer . |
| 4,725,267 | 2/1988 | Vaillancourt . |
| 4,735,618 | 4/1988 | Hagen . |
| 4,737,144 | 4/1988 | Choksi . |
| 4,738,663 | 4/1988 | Bogan . |
| 4,743,233 | 5/1988 | Schneider . |
| 4,747,830 | 5/1988 | Gloyer et al. . |

Primary Examiner—John D. Yasko
Attorney, Agent, or Firm—Brumbaugh, Graves, Donohue & Raymond

[57] ABSTRACT

A user-protective holder for use with a hypodermic syringe comprises a unitary tubular holder member adapted to be received over the syringe barrel, a coupling device for securing the holder member to the finger flanges of the barrel, and a tubular protective sheath received over the barrel in a retracted position in which the needle is exposed for use and movable along the barrel to an extended position in which the needle is received entirely within the sheath such that the sheath protects the user against needle pricks. A releasable latch device couples the sheath to the holder member in the retracted position. The latch device and the coupling device are designed to enable the holder member and sheath to be preassembled to each other before the syringe is inserted into and coupled to the holder member. A spring or a latch device holds the sheath in the extended position.

21 Claims, 5 Drawing Sheets

USER-PROTECTIVE HYPODERMIC SYRINGE HOLDER

This is a continuation-in-part of application Ser. No. 127,689, filed Dec. 2, 1987 now abandoned.

BACKGROUND OF THE INVENTION

While accidental needle pricks from used syringes have long been a hazard to medical personnel, they were not a cause for much concern prior to AIDS. Currently, the risk of accidental needle pricks resulting in the transmission of the AIDS virus is substantial and warrants the use of protective measures beyond the greater care naturally exercised by medical personnel in the handling of syringes and other instruments and devices that come into contact with the blood of patients who may be infected with the AIDS virus.

One protective measure that has been widely proposed since the AIDS virus has become widespread is the use of hypodermic syringes fitted with protective devices. The most common approach is to provide a protective sheath on the syringe that is retracted over the barrel to expose the needle for use and that extends to cover the needle after the syringe has been used. To date, such protective syringes have not come into widespread use. To some extent, the reason for the minimal acceptance of protective syringes may be industrial inertia; there are numerous suppliers of lowcost disposable syringes, and the costs to those suppliers of developing reliable protective syringes, discarding existing tooling for conventional syringes, and acquiring new tooling for protective syringes are considerable. Another reason is probably a degree of inertia on the part of hospitals and other customers of the suppliers, who have long bought conventional disposable syringes and have not yet encountered problems serious enough to cause them to change their purchasing habits. In this regard, the great care now exercised by medical personnel, because of AIDS, in avoiding exposure to patients' blood, appears so far to have been very effective in minimizing instances of the contraction of AIDS.

Most of the proposed protective syringes require modification of the syringe barrel to include latching elements, such as grooves or bosses, for retaining the protective sheath in the retracted position and the extended position. Examples of such latching arrangements are found in U.S. Pat. Nos. 3,890,971 (Leeson et al.); 4,425,120 (Sampson et al.); 4,702,738 (Spencer); 4,737,144 (Choski); and 4,743,233 (Schneider). The provision of such latch elements on the syringe barrel requires more complicated and costly molds and greatly increases the difficulty of holding tolerances in the molded barrel to ensure proper functioning of the latch elements and of the plunger-barrel.

Other approaches to user-protective hypodermic syringes are found in U.S. Pat. Nos. 4,659,330 (Nelson et al.); 4,664,654 (Strauss); 4,725,267 (Vaillancourt); 4,735,618 (Hagen); and 4,747,830 (Gloyer et al.). Except for Gloyer et al., these patents describe and show small needle shields that are difficult to manipulate and require the user to handle a shield that is close to the needle, thus presenting a greater chance of an accidental needle prick in deploying the shield. Gloyer et al. suggest a syringe designed for retraction of the needle into the barrel after use. The latch and coupling elements are complicated and thus difficult and costly to make.

U.S. Pat. No. 4,738,663 (Bogan) describes and shows a needle shield in which a two-piece sleeve guide is attached to the finger flanges of a commercial syringe and a sleeve is assembled onto the guide. The guide has latches that hold the sleeve in a retracted portion for use of the syringe and an extended position in which the needle is covered. The three-part construction requires tedious and time-consuming manipulations to ready the syringe for use, and both latches are releasable. In the case of the extended-position latch, accidental release is possible during handling after use thereby exposing the needle. The design of this latch also makes it subject to malfunction by failure of the projections on the guide to capture the sleeve if it is moved too rapidly to the extended position. Because the extended-position latch is releasable, which is necessary to enable it to be assembled, and because an unused syringe can be at hand ready for use with the sleeve in the extended position and a used syringe can be mistaken for the unused one, there is a significant chance of accidental reuse of a used syringe. It is desirable that unused syringes be clearly identifiable and distinguishable from used syringes and that used syringes not be reusable.

SUMMARY OF THE INVENTION

An object of the present invention is to provide a user-protective holder for a conventional disposable syringe that is easy to use and inexpensive to make and, in particular, a holder that is constructed such that it is fully assembled as supplied to the user and is ready to receive the syringe. A further object is to minimize the possibility of a misuse of the holder and thereby the possibility of an accidental needle prick. Still, another object is to provide a user-protective syringe holder that can be used for syringes of different makers, which vary somewhat in size.

The foregoing and other objects are attained, in accordance with the present invention, by a user-protective syringe holder comprising a unitary tubular holder member adapted to be received over the syringe barrel with a portion closely adjacent the barrel finger flanges, a coupling device for securing the holder member to the finger flanges of the barrel, and a tubular protective sheath received over the barrel in a retracted position in which the needle is exposed for use and movable along the barrel to an extended position in which the needle is received entirely within the sheath such that the sheath protects the user against needle pricks. A releaseable latch device couples the sheath to the holder member in the retracted position. The latch device and coupling device are of a design such that the holder member and sheath can be preassembled to each other before the syringe is inserted into and coupled to the holder member. A spring or a second latch device holds the sheath in the extended position upon release of the latch and movement of the sheath to the extended position.

For a better understanding of the invention, reference may be made to the following description of exemplary embodiments of the invention, taken in conjunction with the accompanying drawings.

DESCRIPTION OF THE DRAWINGS

FIGS. 9 to 12 are views of the sheath of the second embodiment, as follows:

FIGS. 13 to 16 are views of the holder member of the second embodiment, as follows:

FIGS. 17 to 20 show the retainer clip, as follows:

DESCRIPTION OF THE EMBODIMENTS

Figures 1, 2:
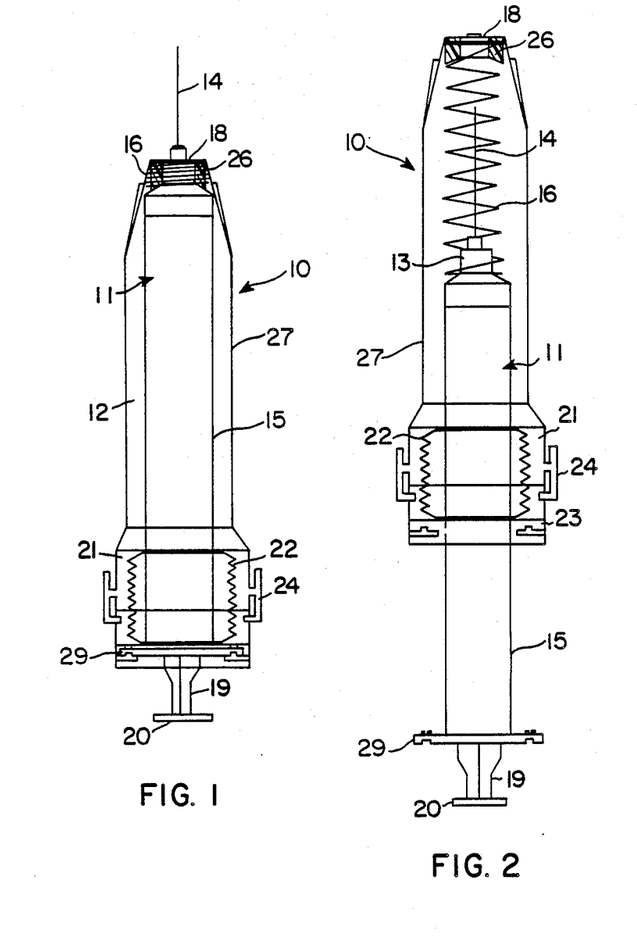
FIG. 1 is a side elevational view of one embodiment of the invention, showing it with the protective sheath of the holder in the retracted position for use of the syringe.
FIG. 2 is a side elevational view of the embodiment of FIG. 1, showing it with the syringe partly received in the holder in the course of being inserted.

In the embodiment of FIGS. 1 to 6, a tubular holder 10 receives a conventional disposable hypodermic syringe 11 having a Luer Lok coupling 13 for a needle 14 at one end of a barrel 15 and a plunger 19 with a finger flange 20 received in the other end of the barrel. The holder 10 includes a unitary tubular holder member 23 that has a bayonet-type coupling arrangement by which it may be attached by insertion and rotation to the finger flange 29 of the syringe barrel 15, rubber inserts 25 being incorporated in the bayonet coupling to ensure the integrity of the connection. The holder 10 further includes a tubular sheath 27 of a diameter somewhat greater than that of the syringe barrel to leave a space 12. An internal flange 26 at the distal end of the sheath provides a seat for a helical compression spring 16 and defines a hole 18 through which the needle 14 extends when the sheath is in its retracted position (FIG. 1). The holder member 23 and sheath 27 are preferably molded from polypropylene, but other polymers are suitable. An expandable bellows member 22, which may be of polyethylene, is secured to an enlarged portion 21 of the sheath 27 and to the holder member 23. Resiliently deflectable latch lugs 23 are molded on opposite sides of the enlarged portion 21 of the sheath and are releasably received in grooves 28 in the holder member 23.

As shown in FIGS. 1 and 2, the latch lugs 24 couple the sheath 27 to the holder member 23, the bellows member 22 being collapsed within the annular space between the syringe barrel and the members 21 and 23. When the latch lugs 24 are released from the notches 28, the sheath and holder member may move apart axially but remain joined together by the bellows member 22, which is extended to accommodate such movement (FIG. 3).

Figure 3:
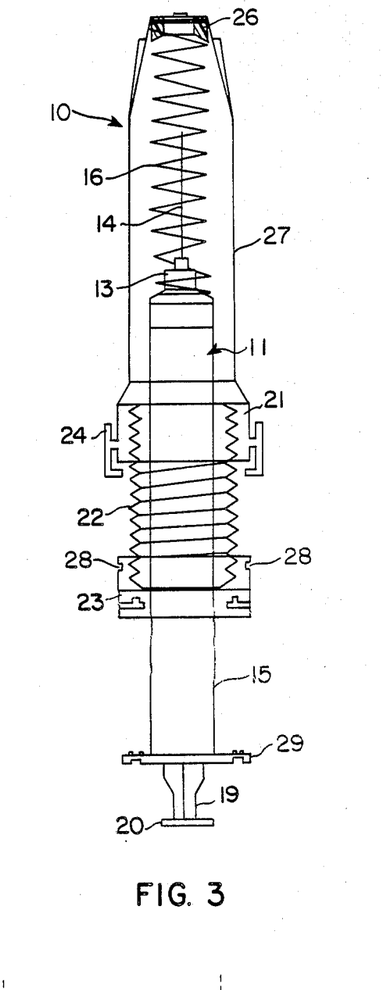
FIG. 3 is another side elevational view of the embodiment of FIG. 1, showing the sheath displaced axially from the holder member.
Figure 4:
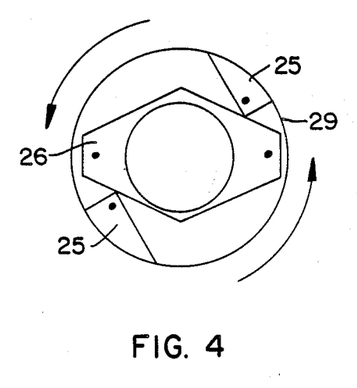
FIG. 4 is a plan view of the plunger end of the embodiment of FIG. 1.
Figure 5:
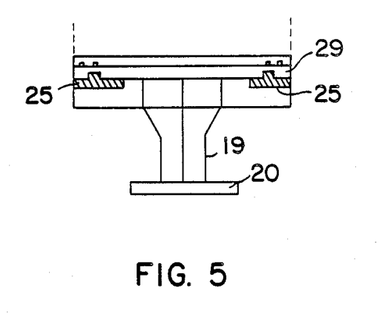
FIG. 5 is a detail side elevational view of the plunger end of the embodiment of FIG. 1.
Figure 6:
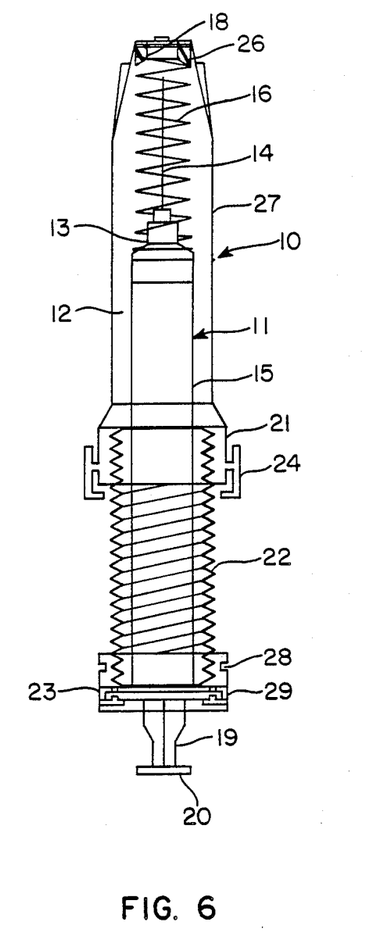
FIG. 6 is a side elevational view of the embodiment of FIG. 1, showing the sheath extended to cover the needle.

As shown in FIGS. 2 and 3, the holder is preassembled and can receive the syringe, which is simply inserted into the holder through the open end of the holder member 23. The holder member and sheath may be latched (FIG. 2) or unlatched (FIG. 3) when the syringe is inserted. Also, the needle may be assembled to the syringe before it is inserted into the holder, or it may be assembled after the syringe is installed. The needle has a needle guard (not shown), which will not be removed until the syringe is to be used.

For use of the syringe, the holder is secured by the bayonet-type coupling of the holder member 23 to the finger flange 29 of the syringe barrel (see FIGS. 1, 4 and 5), and the sheath 27 is latched by the latch lugs 24 to the holder member 23 (see FIG. 1). The spring 16 is compressed into the space around the flange 26.

After the syringe has been used in the usual manner for an injection or for aspiration, the user presses on the latch lugs 24 to dislodge them from the notches 28. If the user merely grips the latch pieces with his/her fingers, the spring 16 will move the syringe 11 and the holder member 23 relative to the sheath 27 to the position shown in FIG. 6, in which the sheath attains its extended position fully enclosing the needle. The bellows member 22 extends but keeps the sheath from separating entirely from the assembly—that is, it acts as a stop. The spring 16 holds the sheath in the extended position (FIG. 6), in which the user (and others) are protected from an accidental needle prick. The syringe and holder can now be disposed of in the usual special disposal receptacle.

Figure 7:
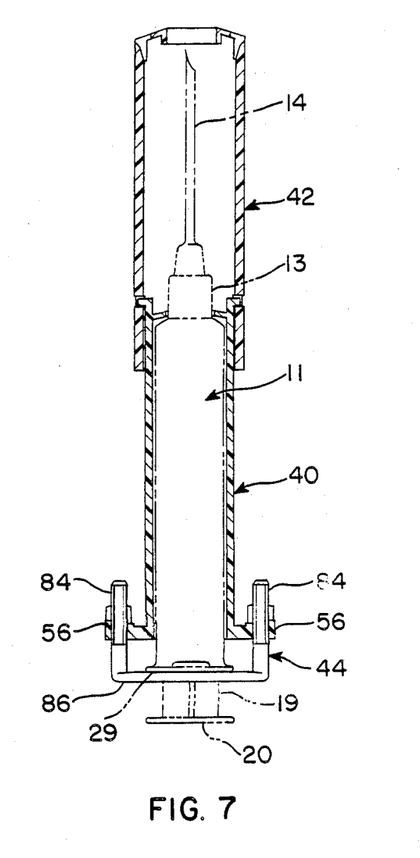
FIG. 7 is a side cross-sectional view of a second embodiment of the invention, showing the sheath in its extended position.
Figure 8:
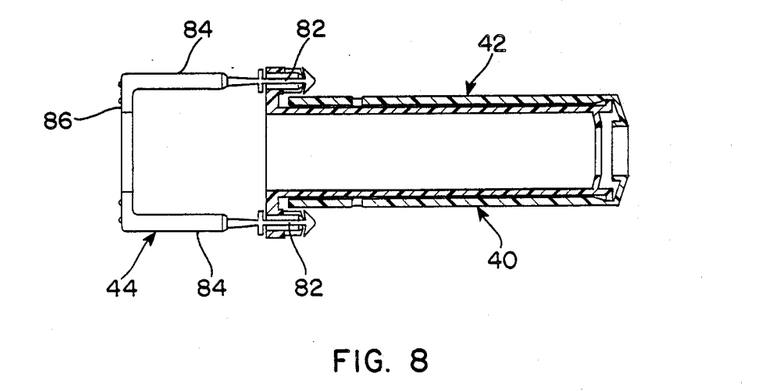
FIG. 8 is a side cross-sectional view of the second embodiment, showing the sheath in its retracted position.
Figure 9:
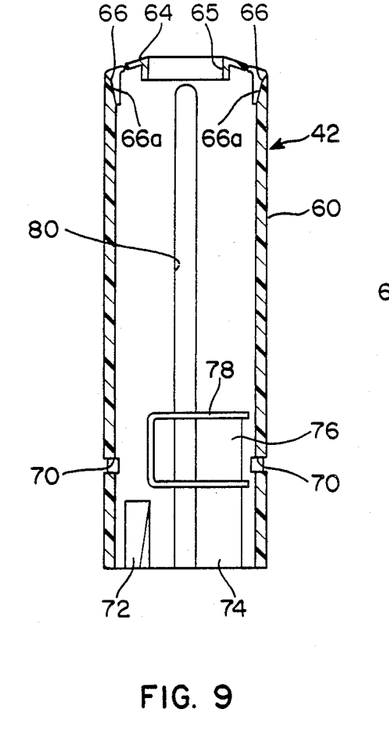
FIG. 9 - side cross-sectional.
Figure 10:
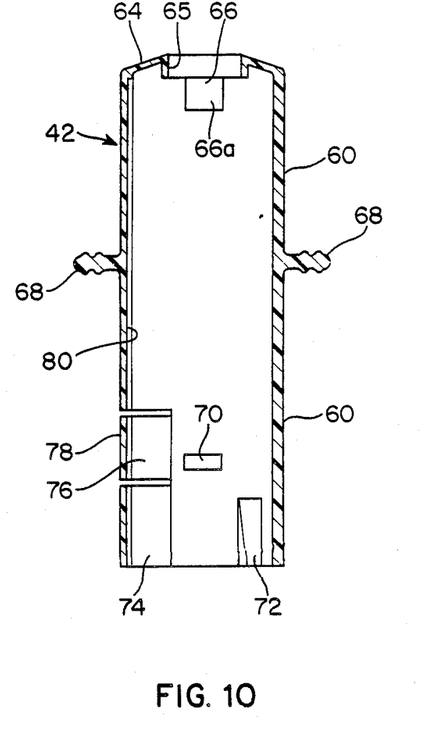
FIG. 10 - side cross-sectional taken orthogonally to FIG. 9.
Figure 11:
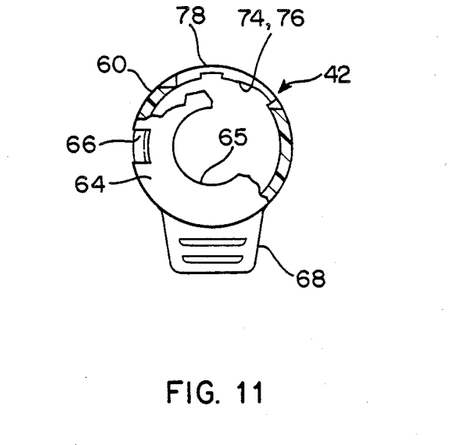
FIG. 11 - plan of the distal (needle) end, partly broken away in section.
Figure 12:
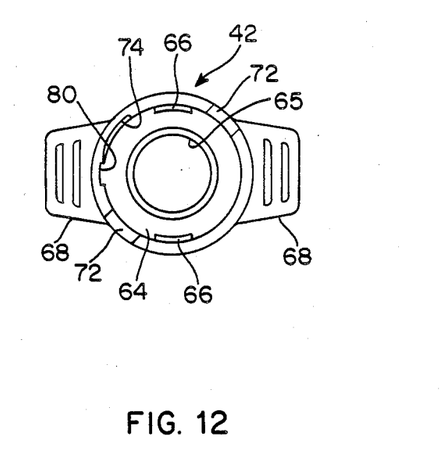
FIG. 12 - plan of the proximal (plunger) end.
Figure 13:
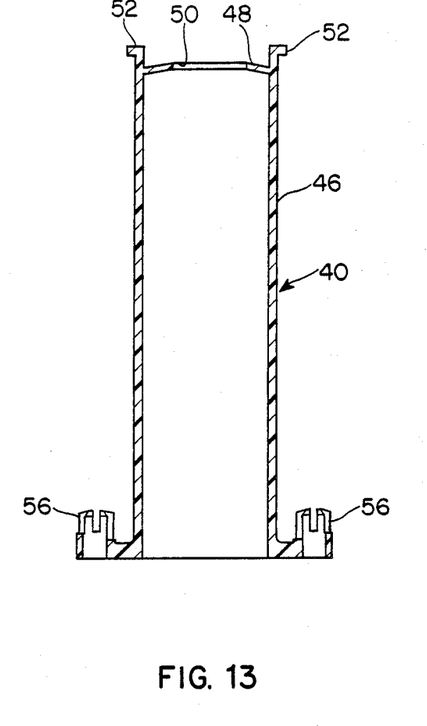
FIG. 13 - side cross-sectional.
Figure 14:
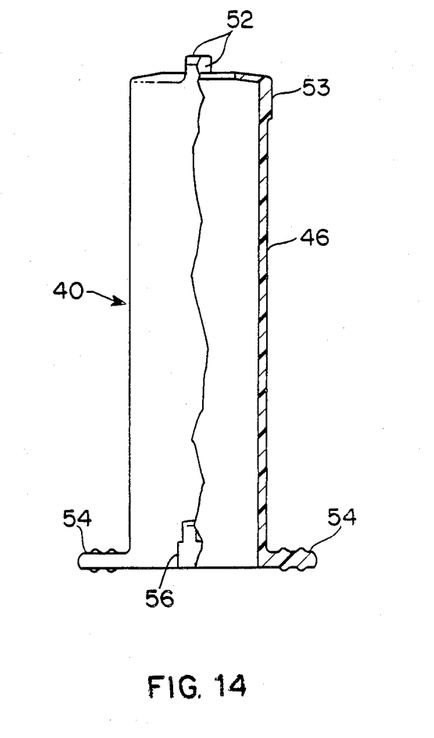
FIG. 14 - side half cross-sectional taken orthogonally to FIG. 13.
Figure 15:
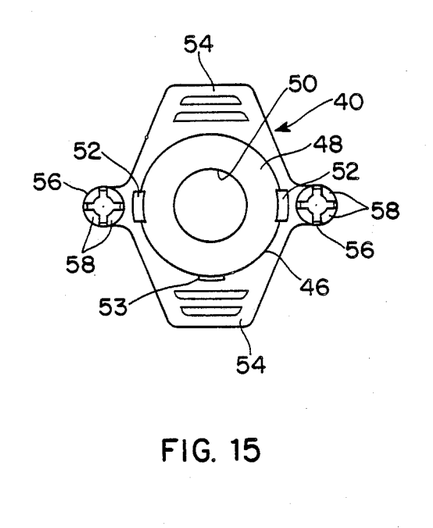
FIG. 15 - plan of the distal (needle) end.
Figure 22:
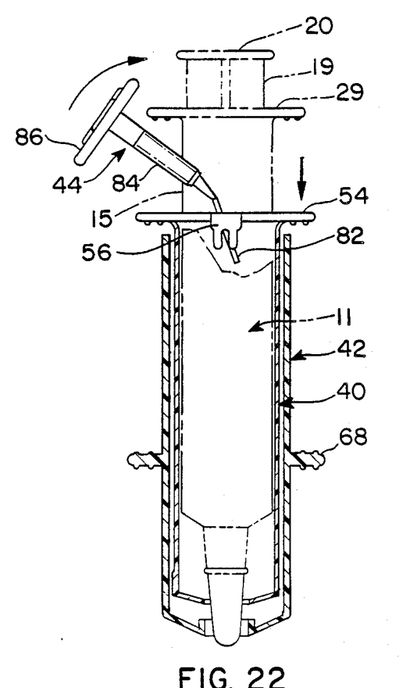
FIG. 22 is a side cross-sectional view of the second embodiment showing how the syringe is installed.

The embodiment of the invention shown in FIGS. 7 to 23 comprises a unitary tubular holder member 40, a tubular sheath 42 and a retainer clip 44 which are adapted to be preassembled and supplied to the user or to a supplier of syringes in the configuration shown in FIG. 8. In that configuration the syringe (which is designated by the numeral 10 and is shown in phantom lines in FIGS. 7, 22 or 23) can be quickly assembled into the holder and secured in place by the retainer clip, as described below. The holder member, sheath and clip are all manufactured inexpensively by injection molding of a suitable polymeric material, such as polypropylene. The sheath and holder member must be transparent or provided with windows so that the dosage markings on the syringe can be seen.

Figure 16:
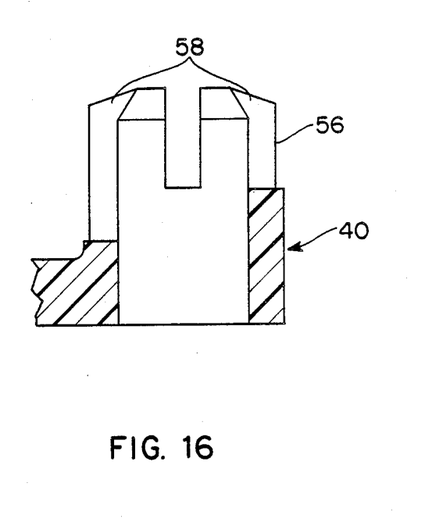
FIG. 16 - cross-sectional detail (enlarged scale) of the sockets for the syringe retainer clip.
Figure 17:
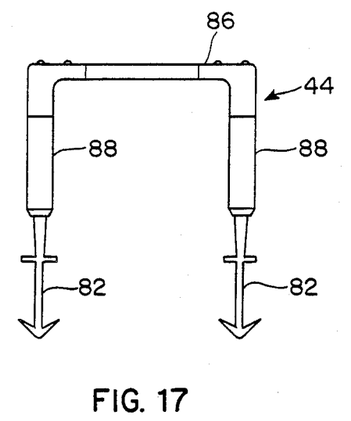
FIG. 17 - side elevational.
Figure 18:
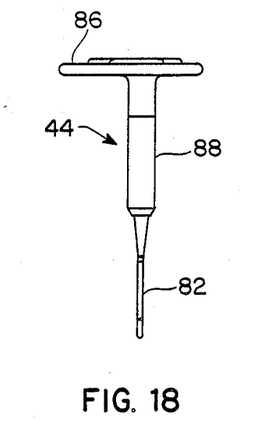
FIG. 18 - end elevational.
Figure 19:
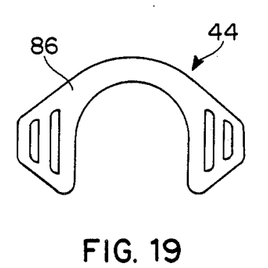
FIG. 19 - top plan.
Figure 20:
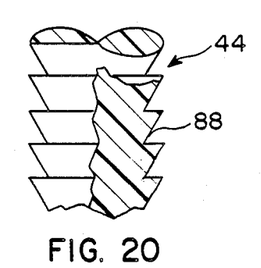
FIG. 20 - detail of ratchet teeth on legs.
Figure 21:
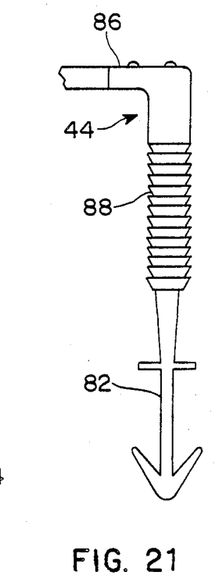
FIG. 21 - partial detail side elevational (larger scale than FIG. 17)

The holder member 40 (FIGS. 13 to 16) comprises a circular cylindrical tubular wall portion 46 of an internal diameter large enough to allow the syringe barrel to be easily slided into it and of a length such as to receive most of the syringe barrel within it. At the distal end is an end wall portion 48 that is engaged by the distal end of the syringe barrel and has a hole 50 through which the Luer Lok coupling of the syringe protrudes when the syringe is in place (see FIG. 23, in which the Luer Lok is capped, as is conventional). Small L-shaped latch lugs 52 extend from the distal edge of the wall 46 at diametrically opposite locations. A small guide boss 53 protrudes from the external surface of the body adjacent the distal end. At the proximal end of the body 46 are diametrically oppositely located finger flanges 54 and diametrically oppositely located retainer sockets 56. The retainer sockets 56 are small tubes with partial cruciform slits forming four resilient deflectable gripping fingers 58 (FIG. 16).

The sheath 42 (FIGS. 9 to 12) has a circular cylindrical tubular wall 60 of an internal diameter such as to be received telescopically over the holder number 40 and to be readily slided lengthwise along the holder member between a retracted position (FIGS. 8 and 23) and an extended position (FIG. 7), and of a length such as to be substantially coextensive with the holder member wall 46. A lengthwise guide groove 62 receives the guide boss 53 on the holder member and prevents the sheath from rotating on the holder member when it is moved between the retracted and the extended positions, thereby to maintain register of the two sets of latches (described below). A distal end wall 64 provides a minimal size opening 65 for protrusion of the syringe Luer Lok coupling and maximum protection against a needle prick when the sheath is extended. Diametrically opposite latch slots 66 at the juncture of the body 60 and the end wall 64 accept the latch lugs 52 of the holder member 50 to retain releasably the sheath 52 in the retracted position (see FIG. 8). The proximal edges 66a of the slots 66 are oblique to the axis of the sheath to facilitate release of the latch lugs 52 by a camming action upon application of a force to the sheath in the distal direction. Pushing the sheath to the extended, user-protective position is facilitated by finger flanges 68 provided for that purpose.

Latch slots 70 in wall 60 of the sheath receive the latch lugs 52 of the holder member when the sheath is extended (FIG. 7). The edges of the notches 70 are orthogonal to the axis of the sheath so that once the lugs 52 are received in them, the latch is essentially non-releasable. Accordingly, when the sheath is extended and latched, the syringe cannot be reused, because the needle is fully sheathed and cannot be unsheathed.

Assembly of the sheath onto the holder member is facilitated by a pair of diametrically opposite internal recesses 72 having inclined surfaces that allow the lugs 52 to enter readily and progressively deflect the lugs inwardly as the holder member is pushed into the sheath. A shallow internal lengthwise recess 74 presented by a thin portion of the wall 60 of the sheath (see FIG. 11) allows the guide boss 53 to enter the holder member. The guide boss 53 then moves onto a contiguous recess portion 76 of a deflectable flap 78 defined by slits along three edges in the wall 60. The recesses 72 and 74 are offset circumferentially from the latch slots 66 and 70 and from a lengthwise internal guide groove 80 in the sheath that receives the guide boss 53 of the holder member. After the holder member has been pushed partway into the sheath far enough to position the boss 53 on the surface 76 of the flap 78, the holder member is rotated relative to the sheath to move the boss 53 along the progressively thicker part of the flap until it snaps into the grooved part of the flap. The flap resiliently deflects as the boss moves along it into the groove. The flap is located lengthwise of the sheath far enough from the proximal end so that the latch lugs 52 are distally beyond the latch notches 70 when the sheath is rotated to its final circumferential position on the holder member; therefore, permanent latching in the extended position cannot occur during assembly. After the rotation of the sheath to located the guide boss 53 in the guide groove 80, the holder member is pushed all the way into the sheath to the retracted position in which the latch lugs 52 are seated in the latch slots 66 (see FIG. 8).

Figure 23:
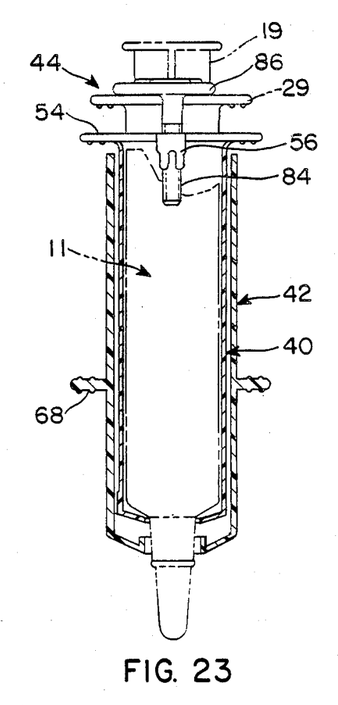
FIG. 23 is a side cross-sectional view showing the syringe fully installed in the holder.

The retainer clip 44 is preassembled to the holder member by reception of anchor-shaped portions 82 on the ends of the legs 84 of the clip in the sockets 58 of the holder member. The anchor portions 82 are easily bent, so a C-shaped head portion 86 and ratchet-toothed portions 88 of the legs 84 can be bent to one side of the holder member to allow the syringe 11 to be inserted into the holder. The anchor portions 82 are located far enough from the head portion 86 to allow the head portion to clear the finger flanges 26 of the syringe barrel. The head portion of the clip 44 straddles the syringe plunger 19. Accordingly, after the syringe is inserted fully into the holder, the retainer clip is bent back to locate the body portion 86 over the syringe flanges. The clip is then pushed down to position the ratchet-toothed portions 88 of the legs 84 in the sockets 56 and engage the head portion 86 of the clip with the finger flanges of the syringe barrel (see FIGS. 22 and 23). The ratchet teeth on the legs of the clip are engaged by the fingers 58 of the sockets 56 and prevent the clip from moving proximally, thus permanently clamping the syringes between the head portion 86 of the clip and the end wall 48 of the holder member 40. The clip self-adjusts to syringes of different lengths. If desired, the anchor portions of the clip can be broken off the legs, as shown in FIG. 23.

After removing the protective cap from the Luer Lok coupling of the syringe and installing the needle, the syringe is used in the conventional manner. After use the user pushes the sheath distally, with the aid of the finger flanges 68, to dislodge the latch lugs 52 by camming action from the latch slots 66 and move the sheath along the holder member to the extended position (FIG. 7). The guide boss 53 and guide groove 80 ensure solely longitudinal movement of the sheath and register of the latch lugs 52 with the latch slots 70 when the sheath arrives at the extended position. The latch lugs reside into the latch slots and permanently hold the sheath in the extended position for protection of the user and others from an accidental needle prick and for prevention of reuse of the syringe.

I claim:

1. A user-protective holder for use with a hypodermic syringe having a barrel, finger flanges projecting out from the barrel adjacent one end thereof and a coupling for receiving a needle at the other end of the barrel, and a plunger received in the barrel, comprising a unitary tubular holder member adapted to be received over the syringe barrel with a proximate portion closely adjacent the gripping flanges and a distal end closely adjacent the distal end of the barrel, leaving the needle substantially fully exposed for use, coupling means including a coupling element engageable with the finger flanges of the barrel for securing the holder member to the syringe barrel, a tubular protective sheath received over the barrel in a retracted position in which the needle is exposed for use and movable along the barrel to an extended position in which the needle is received entirely within the sheath such that the sheath protects the user against needle pricks, releasable latch means for coupling the sheath to the holder member in the retracted position, the latch means and coupling means being adapted to enable the holder member and sheath to be preassembled to each other before the syringe is inserted into and coupled to the holder member, and means for holding the sheath in the extended position upon release of the latch means and movement of the sheath to the extended position.

2. A user-protective holder according to claim 1 wherein the coupling element is a bayonet-type coupling portion of the holder member adapted to accept the gripping flanges of the syringe barrel.

3. A user-protective holder according to claim 1 wherein the coupling element is a retainer clip coupled to the holder member and engagable with the finger flanges of the syringe barrel.

4. A user-protective holder according to claim 3 wherein the retainer clip is adjustably coupled to the holder member.

5. A user-protective holder according to claim 4 wherein the retainer clip includes a generally U-shaped head portion engagable with the finger flanges of the syringe barrel and straddling the syringe plunger and a pair of leg portions, each having ratchet teeth, received in socket portions on the holder member, the socket portions including deformable fingers that enable one-way adjustment of the clip by enabling the ratchet teeth to be moved past the fingers in only one direction.

6. A user-protective holder according to claim 1 wherein the holder member includes outwardly extending finger flanges located adjacent the finger flanges of the syringe when the syringe is installed in the holder such as to facilitate manipulation of the syringe by means of the holder finger flanges.

7. A user-protective holder according to claim 1 wherein the holding means comprises a compression spring engaged between the sheath and the syringe.

8. A user-protective holder according to claim 7 wherein the holder member and sheath are joined by an extensible bellows that is collapsed when the sheath is in the retracted position and is extended when the sheath is in the extended position, the bellows serving to retain the sheath against dislodgement from the assembled holder member and syringe when the sheath is extended by the spring.

9. A user-protective holder according to claim 1 wherein the holding means comprises resiliently deformable lugs on the holder member and slots in the walls of the sheath that receive the lugs when the sheath is in the extended position.

10. A user-protective holder according to claim 9 wherein the latch means comprises said deformable lugs and second slots in the sheath that receive the lugs when the sheath is in the retracted position.

11. A user-protective holder according to claim 1 wherein the latch means comprises resiliently deformable latch lugs on the sheath and grooves on the holder member that receive the lugs when the sheath is in the retracted position.

12. A user-protective holder according to claim 1 wherein the holder member and sheath are substantially coextensive with each other and with the syringe barrel, the sheath being received telescopically outside the holder member in the retracted position, and being slidable along the holder member to the extended position, wherein the coupling means includes a retainer clip having a head position engaging the finger flanges of the syringe barrel and leg portions adjustably coupled to the holder member, and wherein the holder member includes a distal end wall having a hole through which the needle coupling extends and engagable by the distal end wall of the syringe barrel adjacent the needle coupling, whereby the barrel is engaged and held between the retainer clip and the distal and wall of the holder member and whereby the adjustability of the retainer clip (1) enables the retainer clip to be preassembled to the holder member before the syringe is installed and (2) enables syringes of different lengths to be used with the holder.

13. A user-protective holder according to claim 12 wherein the head portion of the retainer clip is generally U-shaped and straddles the syringe plunger and wherein the leg portions have ratchet teeth and are received in socket portions on the holder member, the socket portions including deformable fingers that enable one-way adjustment of the clip by enabling the ratchet teeth to be moved past the fingers in only one direction.

14. A user-protective holder according to claim 12 wherein the latch means includes deformable lugs on the holder member adjacent the distal end and first slots in the sheath that receive the lugs when the sheath is in the retracted position and wherein the holding means includes said deformable lugs on the holder member and second slots in the walls of the sheath that receive the lugs when the sheath is in the extended position.

15. A user-protective holder according to claim 14 wherein the first slots have cam surfaces oblique to the axis of the sheath by which the lugs are dislodged by camming action from the first slots when the sheath is pushed forceably from the retracted position toward the extended position.

16. A user-protective holder according to claim 14 wherein the second slots have edges that are substantially orthogonal to the axis of the sheath such that once the lugs are received in them, they cannot be dislodged and the holder and syringe are rendered essentially unusable after the sheath is moved to the extended position.

17. A user-protective holder according to claim 15 wherein the holder has a guide boss projecting from its outer wall surface and the sheath has a lengthwise guide groove on its inner wall surface receiving the guide boss, whereby the sheath is constrained from rotating relative to the holder member when it is moved from the retracted to the extended position and register of the lugs with the second slots is ensured.

18. A user-protective holder according to claim 12 wherein the sheath has outwardly projecting finger flanges spaced-apart from its ends to facilitate moving the sheath from the latched retracted position to the extended position.

19. A user-protective holder according to claim 17 wherein the end position of the sheath remote from the distal end of the holder member has internally recessed entrance portions that readily accept the lugs and the guide boss of the holder to facilitate assembly of the sheath onto the holder member.

20. A user-protective holder according to claim 19 wherein the entrance portions are offset circumferentially from the guide groove and latch slots so that the latch lugs do not enter the second latch slots upon assembly of the sheath onto the holder member.

21. A user-protective holder according to claim 20 wherein the sheath includes a circumferential segmental resilient flap associated with the entrance portion for the guide boss and including a portion of the guide groove and adapted to deflect upon rotation of the sheath by engagement by the guide boss to facilitate entrance of the guide boss into the guide groove, the flap being located in a position such that the latch lugs are distally beyond the second latch slots when the guide boss engages the flap and the latch lugs therefore cannot enter the second latch slots.

* * * * *